United States Patent
Sanchez et al.

(10) Patent No.: US 10,024,711 B1
(45) Date of Patent: Jul. 17, 2018

(54) SYSTEMS AND METHODS FOR ASSESSING AUDIO LEVELS IN USER ENVIRONMENTS

(71) Applicant: BlueOwl, LLC, Bloomington, IL (US)

(72) Inventors: Kenneth Jason Sanchez, San Francisco, CA (US); Vinay Kumar, San Francisco, CA (US)

(73) Assignee: BlueOwl, LLC, Bloomington, IL (US)

( * ) Notice: Subject to any disclaimer, the term of this patent is extended or adjusted under 35 U.S.C. 154(b) by 10 days.

(21) Appl. No.: 15/659,281

(22) Filed: Jul. 25, 2017

(51) Int. Cl.
*H04R 29/00* (2006.01)
*G01H 3/14* (2006.01)
*H04R 1/10* (2006.01)
*A61B 5/12* (2006.01)

(52) U.S. Cl.
CPC .............. *G01H 3/14* (2013.01); *A61B 5/121* (2013.01); *H04R 1/1083* (2013.01); *H04R 2430/01* (2013.01)

(58) Field of Classification Search
USPC .......... 381/56, 57, 58, 61, 74, 104, 105, 107
See application file for complete search history.

(56) References Cited

U.S. PATENT DOCUMENTS

| | | | |
|---|---|---|---|
| 7,446,674 B2 | 11/2008 | McKenna | |
| 7,903,826 B2 | 3/2011 | Boersma | |
| 8,886,153 B2 | 11/2014 | Velusamy et al. | |
| 9,105,187 B2 | 8/2015 | Aliakseyeu et al. | |
| 9,275,626 B2 | 3/2016 | Benson et al. | |
| 9,509,269 B1 | 11/2016 | Rosenberg | |
| 9,571,057 B2 | 2/2017 | Tomono et al. | |
| 9,609,416 B2 | 3/2017 | Kaller et al. | |
| 2007/0189544 A1 | 8/2007 | Rosenberg | |
| 2016/0071399 A1 | 3/2016 | Altman et al. | |
| 2017/0188166 A1* | 6/2017 | Eberbach | H04R 29/00 |
| 2017/0270905 A1* | 9/2017 | Asada | G10K 11/178 |

* cited by examiner

*Primary Examiner* — Yosef K Laekemariam
(74) *Attorney, Agent, or Firm* — Armstrong Teasdale LLP

(57) ABSTRACT

A computer system may include at least one processor and a non-transitory, tangible, computer-readable storage medium having instructions stored thereon that, in response to execution by the at least one processor, cause the processor to perform operations including: (i) receiving, from a client device associated with a user within a user environment, sound data collected from the user environment; (ii) analyzing the sound data collected from the user environment; (iii) identifying, based upon the analyzing, a noise characteristic associated with the sound data and a duration of the sound data; (iv) comparing the noise characteristic and the duration to a predetermined noise threshold; (v) determining whether the sound data represents unsafe noise conditions based upon the comparison; and/or (vi) notifying the client device when the sound data is determined to represent unsafe noise conditions. The client device may generate an audible, haptic, and/or visible alert in response.

24 Claims, 4 Drawing Sheets

SYSTEMS AND METHODS FOR ASSESSING AUDIO LEVELS IN USER ENVIRONMENTS

FIELD OF THE INVENTION

The present disclosure relates to systems and methods for assessing audio levels in a user environment to alert a user of unsafe conditions for the user's auditory system. More particularly, the present disclosure relates to systems and methods for assessing noise levels in a user environment using a microphone of a mobile communications device and alerting a user of unsafe noise levels to enable the user to take steps to reduce the negative effects of the noise.

BACKGROUND

People are exposed to a variety of sounds depending on the environment the people are located in. Some environments, such as concerts and working environments, may expose people to unsafe levels of noise. That is, the auditory system of a person may be temporarily or permanently damaged by loud and/or prolonged noises. For example, a worker operating heavy machinery may be exposed to unsafe noise levels for extended periods of time that may cause the worker to lose hearing over time. Although the worker may recognize the noise in the working environment is loud and/or unpleasant, the worker may be unaware of the impact that the noise has on the worker's health. As a result, the worker and/or an employer of the worker may not take steps to reduce the negative effects of the noise, such as reducing noise levels in the environment, removing the worker from the environment periodically, and/or providing equipment to the worker (e.g., ear protection) to limit the impact that the noise has on the worker's auditory system.

In addition to workers that work around loud, heavy machinery, some people may not be exposed to loud noises on a daily basis but rather may be exposed to loud noises on a more periodic basis. For example, an office worker may work in a relatively quiet environment, but may enjoy attending loud music concerts in their free time. While attending these loud music concerts, this office worker may be periodically exposed to loud noises that may cause damage to their auditory systems. These types of people may not even be aware of the damage they are experiencing with respect to their auditory systems by attending such events without hearing protection.

BRIEF SUMMARY

The present embodiments relate to systems and methods for assessing noise at a user environment to alert a user of unsafe noise conditions within the user environment. More particularly, the present embodiments relate to systems and methods for assessing sound data at a user environment to identify at least one noise characteristic and duration of the sound data collected at the user environment. The noise characteristic and duration of the sound data may be compared to at least one predetermined noise threshold to determine whether the sound data represents unsafe noise conditions (e.g., noise levels may cause hearing damage to the user) within the user environment. If the sound data is determined to represent unsafe noise conditions, the system may notify a client device associated with the user by sending an alert to the client device. Alternatively, in response to the notification, the client device may generate a visible, audible, and/or haptic alert to inform the user of the unsafe noise conditions.

Accordingly, in one aspect, a computer-based method for assessing noise at a user environment may be provided. The method may be at least partially performed using a sound analysis computing system including at least one processor in communication with at least one memory device. The method may include: (i) receiving, from a client device associated with a user located within a user environment, sound data collected from the user environment; (ii) analyzing the sound data collected from the user environment; (iii) identifying, based upon the analyzing, a noise characteristic associated with the sound data and a duration of the sound data; (iv) comparing the noise characteristic and the duration to a predetermined noise threshold; (v) determining whether the sound data represents unsafe noise conditions based upon the comparison; and/or (vi) notifying the client device by sending an alert when the sound data is determined to represent unsafe noise conditions. Alternatively, the client device may generate at least one of an audible alert, a haptic alert, and a visible alert in response.

In yet another aspect, a computer system for assessing noise at a user environment may be provided. The computer system may include at least one processor and a non-transitory, tangible, computer-readable storage medium having instructions stored thereon that, in response to execution by the at least one processor, cause the processor to perform operations including: (i) receiving, from a client device associated with a user within a user environment, sound data collected from the user environment; (ii) analyzing the sound data collected from the user environment; (iii) identifying, based upon the analyzing, a noise characteristic associated with the sound data and a duration of the sound data; (iv) comparing the noise characteristic and the duration to a predetermined noise threshold; (v) determining whether the sound data represents unsafe noise conditions based upon the comparison; and/or (vi) notifying the client device by sending an alert when the sound data is determined to represent unsafe noise conditions. Alternatively, the client device may generate at least one of an audible alert, a haptic alert, and a visible alert in response.

In yet another aspect, a non-transitory computer readable medium that includes computer executable instructions for assessing noise at a user environment may be provided. When executed by a sound analysis computing system including at least one processor in communication with at least one memory device, the computer executable instructions may cause the sound analysis computing system to: (i) receive, from a client device associated with a user within a user environment, sound data collected from the user environment; (ii) analyze the sound data collected from the user environment; (iii) identify, based upon the analysis, a noise characteristic associated with the sound data and a duration of the sound data; (iv) compare the noise characteristic and the duration to a predetermined noise threshold; (v) determine whether the sound data represents unsafe noise conditions based upon the comparison; and/or (vi) notify the client device by sending an alert when the sound data is determined to represent unsafe noise conditions. Alternatively, the client device may generate at least one of an audible alert, a haptic alert, and a visible alert in response.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein.

Figure 1:
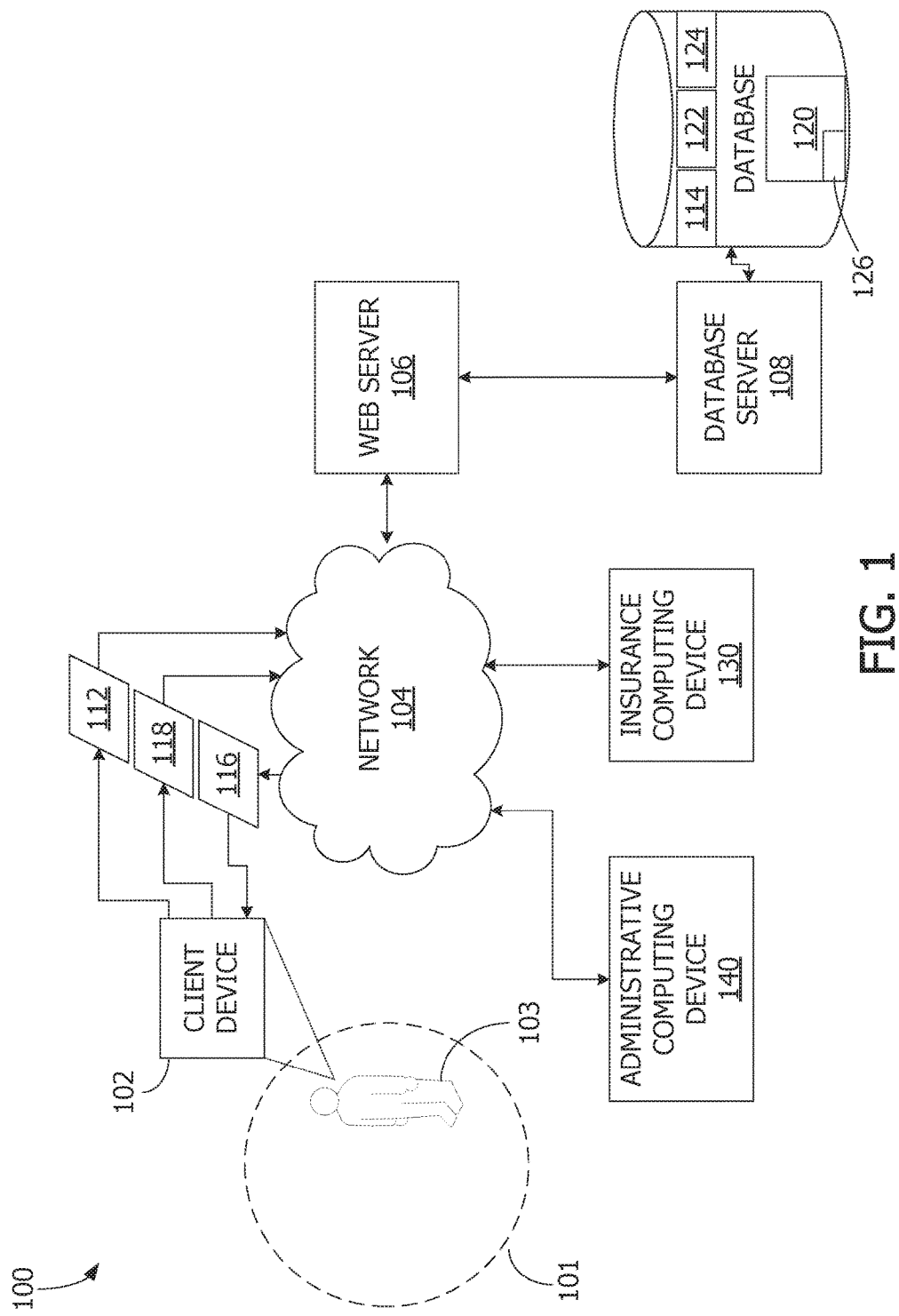
FIG. 1 illustrates a schematic diagram of an exemplary computer system for assessing noise level of noise in a working environment to alert workers of unsafe noise levels.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION OF THE DRAWINGS

The present embodiments may relate to, inter alia, systems and methods for assessing sound at a user environment to alert a user of unsafe noise levels at the user environment. As used herein, a "user environment" may be any suitable environment in which a user is exposed to noise, particularly environments in which the user may be exposed to unsafe noise levels. For example, a user environment may include a user work area, a user home area, an entertainment area visited by the user, an outside area occupied by the user, an inside area occupied by the user, etc. In one exemplary embodiment, the process may be performed by at least one front-end system, such as a client device, and at least one back-end system, such as a web server and/or a database server.

Accordingly, the system may include a client device, such as a personal computer or a mobile communications device. The user may connect to the back-end system (also sometimes referred to herein as a "sound analysis computing system") via the client device to initiate a process for assessing sound at a user environment to alert the user of unsafe noise levels at the user environment. More particularly, the back-end system may deliver a mobile application (e.g., a smartphone "app") to the client device. The smartphone app may assess sound at a user environment, such as a concert, a construction site, a factory, other work areas, and/or any other suitable environment that may include relatively loud noises that is occupied by the user. In addition, and as described below, the back-end system and/or the smartphone app may assess sound over a period of time in a plurality of user environments visited by the user and provide a noise report to the user to evaluate the noise levels the user was exposed to over time.

In various embodiments, the user may keep the client device with himself or herself while the user is present at a particular user environment. The client device may include a microphone and/or other component configured to collect ambient sound data from the user environment when the user is within the user environment. In particular, the smartphone app may cause the client device to record the ambient sound data. In at least some embodiments, the client device may include an analog to digital converter and/or other components that convert analog audio waveforms captured by the client device into digital sound data for analysis as described herein.

The client device may transmit the collected sound data to the back-end system (e.g., the web server and/or the database server) for analysis. In other embodiments, the client device may analyze the collected sound data locally. The sound data may be instantaneous or collected over a duration of time. The analysis may be performed to identify one or more noise characteristics of the sound data. In the exemplary embodiment, the noise characteristics may include, but are not limited to, a maximum decibel level of the sound data, an average decibel level of the sound data, frequency characteristics, amplitude characteristics, and/or other waveform characteristics that may be identified from the sound data. In the exemplary embodiment, the noise characteristics may be quantitative. The duration of the sound data may also be identified during the analysis.

To determine whether or not the user environment associated with the sound data has or had unsafe noise conditions (i.e., the noise levels may cause damage to the user's auditory system and/or other related systems within the body), the back-end system and/or the client device may compare the identified noise characteristics and the duration of the sound data to one or more predetermined noise thresholds. The predetermined noise thresholds may be stored in a database communicatively coupled to the database server and/or in a data storage device of the client device. The predetermined noise thresholds may be variable such that the noise threshold may be a function of time and/or the noise characteristic. For example, the predetermined noise threshold may by lower over extended periods of time relative to the noise threshold over a shorter period of time.

Based upon the comparison, the back-end system and/or the client device may determine whether the user is exposed to unsafe noise conditions within the user environments. The back-end system may notify the client device when the user is determined to be exposed to unsafe noise conditions. The notification may include information associated with the determination, such as how long the user has been exposed to the unsafe noise conditions. In response to the notification, the client device may generate an alert for the user. The alert may be an audible, visible, and/or haptic alert. In at least some embodiments, the alert may be generated by the smartphone app installed on the client device. Additionally and/or alternatively, the alert may be generated by the back-end system. The user may take steps to reduce the negative effects of the unsafe noise conditions in response to the alert, such as reducing the noise generated by an object or person, leaving the user environment, and/or equipping audio safety equipment (e.g., ear plugs).

In some embodiments, the back-end system and/or the client device may be configured to facilitate assessing noise conditions associated with a user over extended periods of time and/or through different user environments. The back-end system and/or the client device may provide a noise report to the user to enable the user to analyze how often the user is exposed to unsafe noise conditions and assess the associated health risk. A noise report is a set of organized data associated with sound data over a predefined duration of time that indicates when the user was exposed to unsafe noise conditions. In certain embodiments, the noise report may include one or more graphical elements (e.g., charts, graphs, tables, etc.) to display the organized data.

The user may opt-in to the noise report to permit the smartphone app to collect sound data over extended periods of time. In some embodiments, the user may specify the total duration of time to be included in the noise report. In other embodiments, the client device and/or the back-end system may automatically determine the duration of time to be included in the noise report. The sound data may be analyzed similar to the sound data collected from a single user environment, and alerts identifying unsafe noise conditions may continue to be transmitted while collecting the sound data for the noise report. A log of alerts associated with the user and/or the client device may be stored in a database to evaluate how often the user receives the alerts.

In some embodiments, the client device may collect location data while collecting the sound data. The client device may include a location module for collecting location data, such as, and without limitation, Global Positioning System (GPS) data. The location data may be used to determine which user environment the user was located in. More specifically, the location data may be synchronized with the sound data with respect to time so as to enable association of portions of the sound data with particular user environments. In at least some embodiments, a particular user environment may be associated with a portion of the sound data by determining the user was located at the user environment during a time increment of the total duration that is associated with the portion of the sound data. The location data may be stored by the client device and/or the database communicatively coupled to the back-end system.

In some embodiments, the noise report may include a comparison between the user and other users. More specifically, sound data may be collected for other users and may be transmitted to the back-end system for analysis. The back-end system may identify respective noise characteristics and/or durations from each instance of sound data. The respective noise characteristics and/or durations may then be aggregated to generate aggregated noise characteristics and an aggregated duration. The back-end system may use any suitable aggregation techniques to generate the aggregated noise characteristics and the aggregated duration, such as averaging, normalizing, extrapolating, and/or combinations thereof. In some embodiments, the aggregated duration matches the duration of the sound data associated with the user such that the aggregated noise characteristics represent the same time scale as the sound data of the user. The aggregated noise characteristics and/or the aggregated duration are compared to the sound data of the user to determine how the noise conditions experienced by the user compare to the noise conditions experienced by other users. In certain embodiments, one or more comparison metrics (e.g., percentiles) may be generated based upon the comparison. The noise report may include the comparison metrics and/or other information from the comparison.

The client device and/or the back-end system may generate the noise report based at least partially upon the collected sound data and/or location data and provide the noise report to the user. The back-end system may transmit the noise report to the client device for display within the smartphone app. In some embodiments, the noise report and/or the alerts may be transmitted to an insurance computing device. The insurance computing device may be associated with an insurance provider. The noise report and/or the alerts may be used to assess risks associated with the user and/or to maintain an updated health record for the user. In one example, when determining vehicle insurance coverage for the user, the insurance computing device and/or an insurance agent operating the insurance computing device assess the noise report to determine an extent of the coverage to be provided to the user.

In certain embodiments, the user may permit the noise report and/or alerts to be transmitted to an administrative device. The administrative device may be associated with an administrative party that manages and/or assess one or more user environments. In one example, the administrative device may be associated with an employer of the user and may be configured to assess noise conditions for each worker within a working environment. The administrative party may receive noise reports and/or alerts for multiple users to enable the administrative party to make decisions to reduce the negative effects of unsafe noise conditions. For example, the administrative party may adjust operation of one or more devices to reduce noise, provide noise safety equipment to affected users, and/or rotate workers away from environments with unsafe noise levels periodically.

Exemplary technical effects of the systems, methods, and computer-readable media described herein may include, for example: (a) receiving, from a client device associated with a user, sound data collected from a user environment, wherein the user is located within the user environment; (b) analyzing the sound data collected from the user environment; (c) identifying, based upon the analyzing, a noise characteristic associated with the sound data and a duration of the sound data; (d) comparing the noise characteristic and the duration to a predetermined noise threshold; (e) determining whether the sound data represents unsafe noise conditions based upon the comparison; and/or (f) notifying the client device when the sound data is determined to represent unsafe noise conditions, wherein the client device generates at least one of an audible alert, a haptic alert, and a visible alert in response.

The technical effect achieved by this system may be at least one of: (i) increased awareness of unsafe noise conditions; (ii) proactive actions take to reduce unsafe noise conditions; (iii) improved assessment of noise conditions over time and/or in different locations; and/or (iv) improved identification of unsafe noise conditions by comparing sound data associated with a user to aggregated sound data associated with other users.

Exemplary System for Assessing Sound within a Vehicle and to Alert the Driver

FIG. 1 depicts a view of an exemplary system 100 for assessing noise at a user environment 101 to alert a user 103 that he or she is exposed to unsafe noise levels. User environment 101 may be any suitable environment in which user 103 may be exposed to noise, and in particular, noise that may damage the hearing of user 103. In one exemplary embodiment, system 100 may include a client device, such as a client device 102. Client device 102 may be associated with user 103. System 100 may also include network 104, a web server 106, a database server 108, and/or a database 110.

Accordingly, in the exemplary, client device 102 may be any personal computing device and/or any mobile communications device of a user, such as a personal computer, a tablet computer, a smartphone, and the like. Client device 102 may, as described below, include one or more microphones and may be configured to display a software application (e.g., a smartphone "app"), which may be configured to receive, or "listen to" sound, such as ambient noise, within user environment 101. To this end, client device 102 may include or execute software for viewing and interacting with a smartphone app that receives or listens to sound within user environment 101.

Network 104 may be any electronic communications system, such as any computer network or collection of computer networks, and may incorporate various hardware and/or software. Communication over network 104 may be accomplished via any suitable communication channels, such as, for example, one or more telephone networks, one or more extranets, one or more intranets, the Internet, one or more point of interaction devices (e.g., point of sale devices, smart phones, cellular phones), various online and/or offline communications systems, such as various local area and wide area networks, and the like.

Web server 106 may be any computer or computer system that is configured to receive and process data, such as sound data 112, transmitted by and received from client device 102. Sound data 112 may be analog and/or digital signals representing noise captured by client device 102 from user environment 101. Web server 106 may be coupled between client device 102 and database server 108. More particularly, web server 106 may be communicatively coupled to client device 102 via network 104. In various embodiments, web server 106 may be directly coupled to database server 108 and/or communicatively coupled to database server 108 via a network, such as network 104. Web server 106 may, in addition, function to store, process, and/or deliver one or more web pages and/or any other suitable content to client device 102. Web server 106 may, in addition, receive data, such as sound data 112 provided to the smartphone app (as described herein) from client device 102 for subsequent transmission to database server 108.

In various embodiments, web server 106 may implement various hardware and/or software, such as, for example, one or more communication protocols, one or more message brokers, one or more data processing engines, one or more servlets, one or more application servers, and the like. For instance, in one embodiment, web server 106 may implement web server 106 may implement a message broker program module configured to translate a message or communications from a messaging protocol of a sending device to a messaging protocol of a receiving device (e.g., RABBITMQ, KAFKA, ACTIVEMQ, KESTREL). Further still, in some embodiments, web server 106 may implement a data processing engine, such as a cluster computing framework like APACHE SPARK. In addition, in various embodiments, web server 106 may implement servlet and/or JSP server, such as APACHE TOMCAT.

Database server 108 may be any computer or computer program that provides database services to one or more other computers or computer programs. In various embodiments, database server 108 may be communicatively coupled between web server 106 and database 110. Database server 108 may, in addition, function to process data received from web server 106, such as sound data, which may include, for example, sound data 112 received from client device 102.

In various embodiments, web server 106 and/or database server 108 may implement one or more machine learning algorithms, as described herein, to process sound data, such as sound data 112 stored within database 110. For example, in some embodiments, web server 106 and/or database server 108 may process sound data 112 to identify one or more noise characteristics associated with sound data 112. Such characteristics may include, for example, maximum noise level (e.g., maximum decibel level), average noise level, frequency characteristics, amplitude characteristics, and/or any other waveform characteristics of sound data 112. In some embodiments, web server 106 and/or database server 108 may identify a duration of sound data 112 as well.

Database 110 may be any organized collection of data, such as, for example, any data organized as part of a relational data structure, any data organized as part of a flat file, and the like. Database 110 may be communicatively coupled to database server 108 and may receive data from, and provide data to, database server 108, such as in response to one or more requests for data, which may be provided via a database management system (DBMS) implemented on database server 108. In various embodiments, database 110 may be a non-relational database, such as an APACHE HADOOP database.

In the exemplary embodiment, database 110 may store sound data 112 and/or one or more predetermined noise thresholds 114. Client device 102, web server 106, and/or database server 108 may compare the identified noise characteristics and/or duration of sound data 212 to noise thresholds 114 to determine whether or not user 103 is exposed to unsafe noise conditions (i.e., the ambient noise of user environment 101 may cause hearing damage to user 103). In one example, multiple noise thresholds 114 may be provided to identify a plurality of noise conditions (e.g., safe, potentially unsafe, and unsafe). In at least some embodiments, noise thresholds 114 may be vary at least partially as a function of a noise characteristic (e.g., decibel level) and/or time. In other embodiments, sound data 112 and/or noise thresholds 114 may be stored locally by client device 102, web server 106, and/or database server 108.

When it is determined user 101 is and/or has been exposed to unsafe noise conditions, an alert may be generated by client device 102 to inform user 103 of the unsafe noise conditions. The alert may be a visible, audible, and/or haptic alert. In some embodiments in which web server 106 and/or database server 108 compare sound data 112 to noise thresholds 114, a notification 116 may be transmitted to client device 102 via network 104 to indicate the unsafe noise conditions. Client device 102 may provide the alert to user 103 in response to notification 116. In some embodiments, notification 116 may be the alert, and client device 102 may provide notification 116 to user 103.

In some embodiments, client device 102 may collect and/or transmit location data 118. Location data 118 may be synchronized with sound data 112 with respect to time such that a location of user 103 and corresponding noise levels or other noise characteristics are matched together. Location data 118 may be transmitted with sound data 112 or separately to web server 106 for storage. Location data 118 may be used in particular to evaluate noise characteristics of sound data 112 when user 103 travels to different user environments 101 and/or an event occurs at user environment 101 (e.g., heavy machinery is activated within environment 101).

In at least some embodiments, client device 102, web server 106, and/or database server 108 may generate a noise report 120 associated with a particular user 103. Noise report 120 may be a collection of data associated with user 103 and the noise conditions user 103 may be exposed to over time. In some embodiments, user 103 may opt-in to enable client device 102 to collect sound data 112 and/or location data 118 over a predefined period of time. Sound data 112 and/or location data 118 may be stored by client device 102 and/or database 110. Client device 102, web server 106, and/or database server 108 may identify any increments of the total duration in which the noise conditions associated with user 103 are determined to be unsafe.

In some embodiments, sound data 112 may be compared to sound data associated with other users to determine whether or not user 103 has been exposed to a relatively high or a relatively low amount of unsafe noise conditions. In the exemplary embodiment, sound data associated with other users from other client devices may be transmitted to web server 106 and/or database server 108 via network 104. Web server 106 and/or database server 108 may generate aggregated noise characteristics 122 and/or an aggregated duration 124 based upon the sound data associated with the other users. Aggregated noise characteristics 122 and/or aggregated duration 124 may be generated using any suitable aggregation techniques, such as, and without limitation, averaging, normalizing, extrapolating, and/or combinations thereof. Aggregated noise characteristics 122 and/or aggregated duration 124 may be stored within database 110. In some embodiments, aggregated duration 124 may match the duration of sound data 112 to facilitate comparing aggregated noise characteristics 122 to the noise characteristics of sound data 112 on the same time scale. Web server 106 and/or database server 108 may compare sound data 112 to aggregated noise characteristics 122 and/or aggregated duration 124 and include information associated with the comparison in noise report 120. In some embodiments, web server 106 and/or database server 108 may generate comparison metrics 126 based on the comparison. Comparison metrics 126 may provide a quantitative ranking of the noise conditions experienced by user 103 relative to the other users.

Upon generating noise report 120, web server 106 and/or database 108 may transmit noise report 120 to client device 102 for user 103 to review. User 103 may take steps to reduce the amount of unsafe noise conditions experienced by user 103 based upon review of noise report 120. In some embodiments, noise report 120 may be transmitted to an insurance computing device 130 for assessing risk associated with user 103 and/or to maintain an updated health record for user 103. Additionally or alternatively, noise report 120 may be transmitted to an administrative computing device 140. Administrative computing device 140 may be associated with an administrative party that manages and/or assesses user environment 101. In one example, user environment 101 may be a work environment (e.g., a factory or a construction site), user 103 may be a worker, and the administrative party may be an employer of user 103. The employer may assess conditions associated with a plurality of workers within environment 101 to manage the health of the workers and/or to adjust operation of devices within environment 101 to manage the noise levels. In the exemplary embodiment, user 103 may opt-in to sharing noise report 120 with insurance computing device 130 and/or administrative computing device 140 such that noise report 120 may not be transmitted to insurance computing device 130 and/or administrative computing device 140 without permission from user 103.

Although the components of system 100 are described below and depicted at FIG. 1 as being interconnected in a particular configuration, it is contemplated that the systems, subsystems, hardware and software components, various network components, and database systems described herein may be variously configured and interconnected and may communicate with one another within system 100 to facilitate the processes and advantages described herein. For example, although a single web server 106, a single database server 108, and a single database 110 are described above, it will be appreciated that system 100 may include any suitable number of interconnected, communicatively coupled, web servers, database servers, and/or databases. Further, although certain functions, processes, and operations are described herein with respect to one or more system components, it is contemplated that one or more other system components may perform the functions, processes, and operations described herein.

Exemplary Client Device

Figure 2:
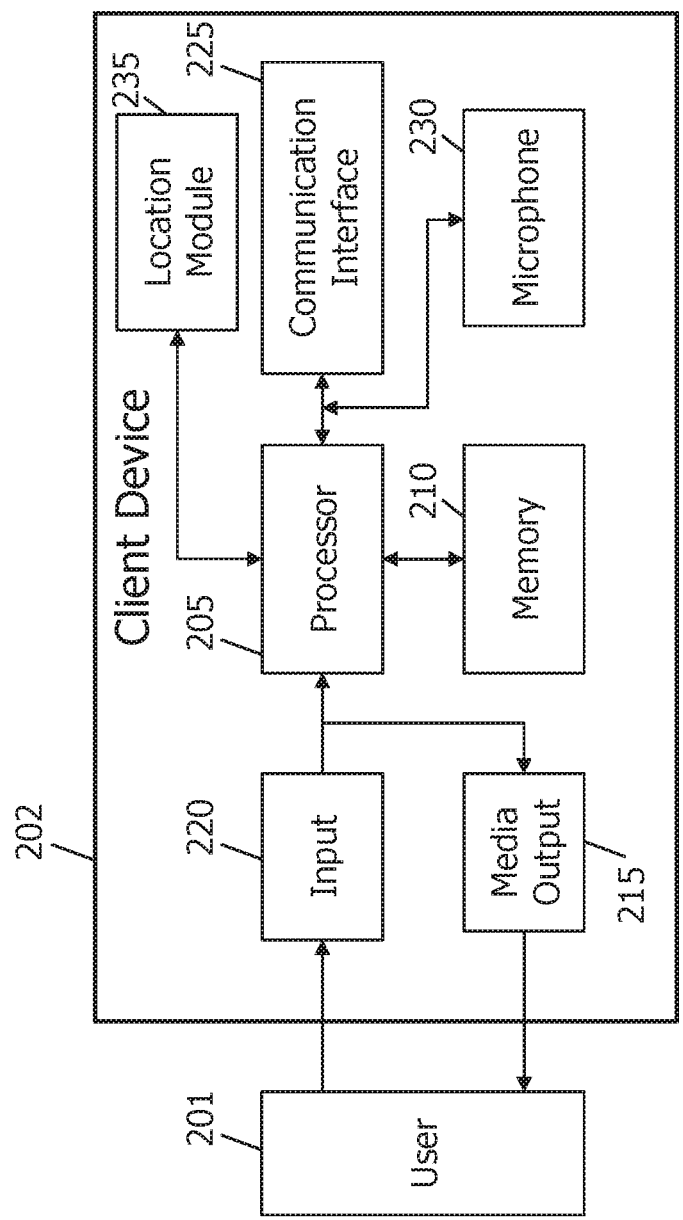
FIG. 2 illustrates an exemplary configuration of a client device shown in FIG. 1, in accordance with one embodiment of the present disclosure.

FIG. 2 depicts an exemplary configuration of a client device 202, such as client device 102, as shown in FIG. 1, and in accordance with one embodiment of the present disclosure. Client device 202 may be operated by a user 201. Client device 202 may include a processor 205 for executing instructions. In some embodiments, executable instructions may be stored in a memory area 210. Processor 205 may include one or more processing units (e.g., in a multi-core configuration). Memory area 210 may be any device allowing information such as executable instructions and/or transaction data to be stored and retrieved. Memory area 210 may include one or more computer readable media.

Client device 202 may also include at least one media output component 215 for presenting information to user 201. Media output component 215 may be any component capable of conveying information to user 201. In some embodiments, media output component 215 may include an output adapter (not shown) such as a video adapter and/or an audio adapter. An output adapter may be operatively coupled to processor 205 and adapted to operatively couple to an output device such as a display device (e.g., a cathode ray tube (CRT), liquid crystal display (LCD), light emitting diode (LED) display, or "electronic ink" display) or an audio output device (e.g., a speaker or headphones).

In some embodiments, media output component 215 may be configured to present a graphical user interface (e.g., a web browser and/or a client application) to user 201. A graphical user interface may include, for example, an online interface for viewing alerts and/or noise reports. In some embodiments, client device 202 may include an input device 220 for receiving input from user 201. User 201 may use input device 220 to, without limitation, select and/or enter data, such as, for example, one or more report criteria or report filters.

Input device 220 may include, for example, a keyboard, a pointing device, a mouse, a stylus, a touch sensitive panel (e.g., a touch pad or a touch screen), a gyroscope, an accelerometer, a position detector, a biometric input device, and/or an audio input device. A single component such as a touch screen may function as both an output device of media output component 215 and input device 220.

Client device 202 may also include a communication interface 225, communicatively coupled via network 104 to web server 106 (shown in FIG. 1). Communication interface 225 may include, for example, a wired or wireless network adapter and/or a wireless data transceiver for use with a mobile telecommunications network.

Stored in memory area 210 are, for example, computer readable instructions for providing a user interface to user 201 via media output component 215 and, optionally, receiving and processing input from input device 220. A user interface may include, among other possibilities, a web browser and/or a client application. Web browsers enable users, such as user 201, to display and interact with media and other information typically embedded on a web page or a website.

Client device 202 may also include one or more microphones, such as microphone 230. Microphone 230 may be any suitable microphone for receiving and/or collecting sound data within user environment 101. Microphone 230 may be communicatively coupled to processor 205, which may implement an analog to digital converter in software to convert analog sound data received by microphone 230 to digital data. In some embodiments, client device 202 may include a separate (e.g., hardware and/or software) analog to digital converter coupled between microphone 230 and processor 205.

In at least some embodiments, client device 202 may also include a location module 235. Location module 235 may capture location data that represents a location of client device 202. The location data may be, for example, GPS data. Location module 235 may include any suitable components for collecting location data and transmitting the location data to processor 205, such as, and without limitation, antennas, amplifiers, switches, signal generators, and/or other components.

Exemplary Database System

Figure 3:
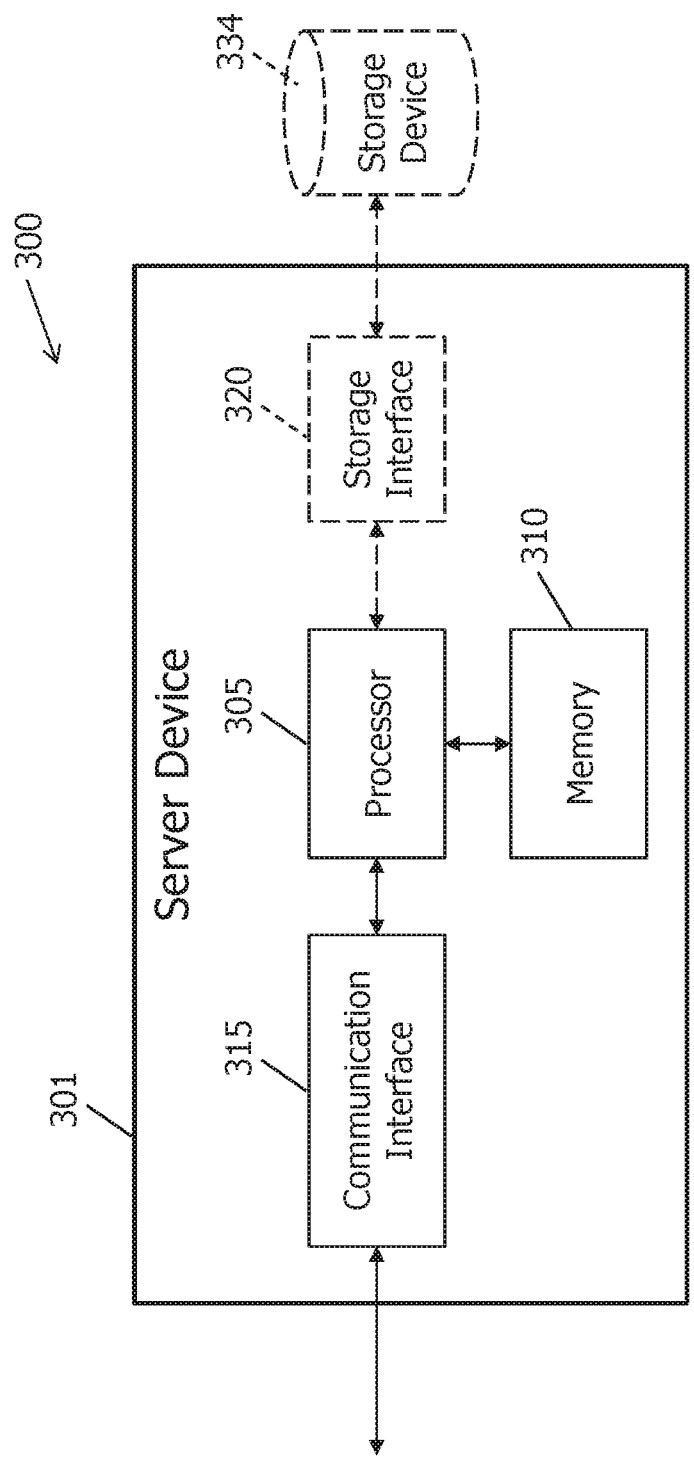
FIG. 3 illustrates an exemplary configuration of a server shown in FIG. 1, in accordance with one embodiment of the present disclosure.

FIG. 3 depicts an exemplary database system 300 such as database server 108 and database 110, as shown in FIG. 1, and in accordance with one exemplary embodiment of the present disclosure. Accordingly, database system 300 may include a server computer device 301 (e.g., database server 108), which may, in turn, include a processor 305 for executing instructions. Instructions may be stored in a memory area 310. Processor 305 may include one or more processing units (e.g., in a multi-core configuration).

Processor 305 may be operatively coupled to a communication interface 315 such that server computer device 301 is capable of communicating with a remote computing device, as described above. For example, communication interface 315 may receive requests from client device 202 via the Internet and/or over a computer network.

Processor 305 may also be operatively coupled to a storage device 334 (e.g., database 110). Storage device 334 may be any computer-operated hardware suitable for storing and/or retrieving data, such as, but not limited to, data associated with database 110. In some embodiments, storage device 334 may be integrated in server computer device 301. For example, server computer device 301 may include one or more hard disk drives as storage device 334.

In other embodiments, storage device 334 may be external to server computer device 301 and may be accessed by a plurality of server computer devices 301. For example, storage device 334 may include a storage area network (SAN), a network attached storage (NAS) system, and/or multiple storage units such as hard disks and/or solid state disks in a redundant array of inexpensive disks (RAID) configuration.

In some embodiments, processor 305 may be operatively coupled to storage device 334 via a storage interface 320. Storage interface 320 may be any component capable of providing processor 305 with access to storage device 334. Storage interface 320 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 305 with access to storage device 334.

Figure 4:
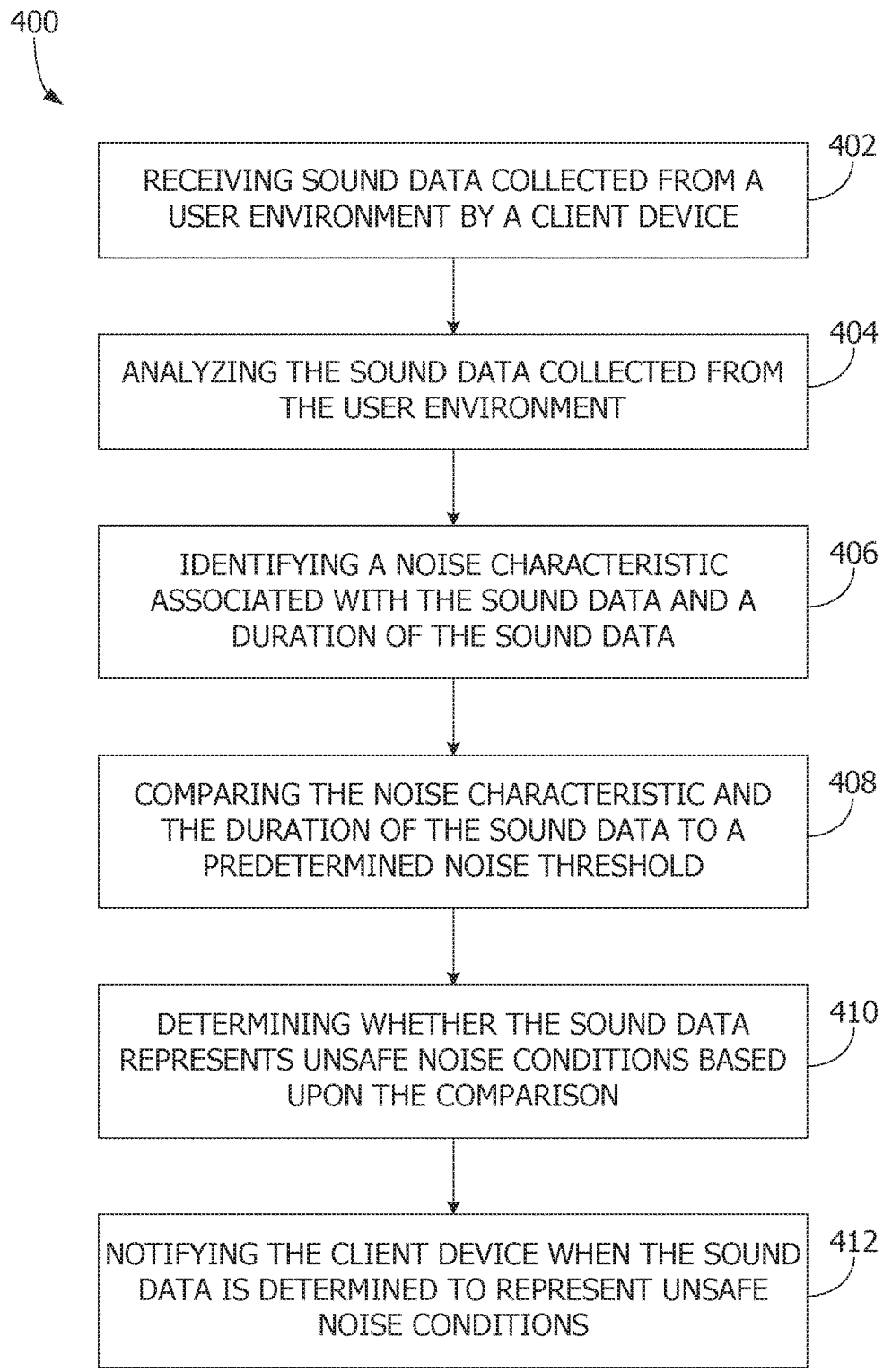
FIG. 4 illustrates an exemplary process implemented by the computer system shown in FIG. 1 for assessing noise levels of noise in a working environment to alert workers of unsafe noise levels.

Exemplary Process for Assessing Noise Levels at a User Environment and to Alert a User FIG. 4 depicts a flowchart of an exemplary process 400 implemented by the computer system shown in FIG. 1 for assessing noise levels at a user environment to alert a user of unsafe noise conditions. Accordingly, in in the exemplary embodiment, system 100 (e.g., web server 106 and/or database server 108) may receive 402 sound data 112 collected from user environment 101 by client device 102. Sound data 112 may be stored in database 110 and may include digital and/or analog sound data associated with ambient noise around user 103 captured by client device 102.

System 100 may analyze 404 sound data 112 and identify 406 one or more noise characteristics associated with sound data 112 and a duration of sound data 112 based upon the analysis. The noise characteristics may include, for example, a maximum and/or an average decibel level of sound data 112. System 100 may be configured to perform any suitable audio identification techniques to identify the noise characteristics and/or the duration of sound data 112. System 100 may then compare 408 the identified noise characteristics and duration to a predetermined noise threshold 114. Noise threshold 114 may be stored in database 110 and/or may vary at least partially as a function of time and/or noise characteristic (e.g., decibel level). Based upon the comparison, system 100 may determine 410 whether sound data 112 represents unsafe noise conditions within user environment 101. In one example, if the decibel level of sound data 112 exceeds noise threshold 114, sound data may represent unsafe noise conditions. System 100 may then notify 412 client device 102 when sound data 112 is determined to represent unsafe noise conditions. In response to notification 116, client device 102 may generate a visible, audible, and/or haptic alert to inform user 103 of the unsafe noise conditions.

In some embodiments, system 100 may receive location data 118 from client device 102. Location data 118 may be synchronized with sound data 112 with respect to time to facilitate evaluating sound data 112 in different user environments 101. System 100 may collect sound data associated with other users to generate aggregated noise characteristics 122 and/or aggregated duration 124 for comparison with sound data 112. Comparing sound data 112 with aggregated noise characteristics 122 and/or aggregated duration 124 may provide a quantitative analysis of the noise conditions experienced by user 103 relative to other users. In certain embodiments, system 100 may receive sound data 112 associated with user 103 over an extended period of time (e.g., one day, one week, one month, etc.) and may generate noise report to enable user 103 and/or others to review the noise conditions experienced by user 103. Noise report 120 may be stored in database 110 and may be updated periodically within database 110.

Exemplary Embodiments & Functionality

In one aspect, a computer-based method for assessing noise at a user environment may be provided. The method may be at least partially performed using a sound analysis computing system including at least one processor in communication with at least one memory device. The method may include: (i) receiving, from a client device associated with a user located within a user environment, sound data collected from the user environment; (ii) analyzing the sound data collected from the user environment; (iii) identifying, based upon the analyzing, a noise characteristic associated with the sound data and a duration of the sound data; (iv) comparing the noise characteristic and the duration to a predetermined noise threshold; (v) determining whether the sound data represents unsafe noise conditions based upon the comparison; and/or (vi) notifying the client device by sending an alert when the sound data is determined to represent unsafe noise conditions. Alternatively, the client device may generate at least one of an audible alert, a haptic alert, and a visible alert in response.

In yet another aspect, a computer system for assessing noise at a user environment may be provided. The computer system may include at least one processor and a non-transitory, tangible, computer-readable storage medium having instructions stored thereon that, in response to execution by the at least one processor, cause the processor to perform operations including: (i) receiving, from a client device associated with a user within a user environment, sound data collected from the user environment; (ii) analyzing the sound data collected from the user environment; (iii) identifying, based upon the analyzing, a noise characteristic associated with the sound data and a duration of the sound data; (iv) comparing the noise characteristic and the duration to a predetermined noise threshold; (v) determining whether the sound data represents unsafe noise conditions based upon the comparison; and/or (vi) notifying the client device by sending an alert when the sound data is determined to represent unsafe noise conditions. The client device may generate at least one of an audible alert, a haptic alert, and a visible alert in response.

In yet another aspect, a non-transitory computer readable medium that includes computer executable instructions for assessing noise at a user environment may be provided. When executed by a sound analysis computing system including at least one processor in communication with at least one memory device, the computer executable instructions may cause the sound analysis computing system to: (i) receive, from a client device associated with a user within a user environment, sound data collected from the user environment; (ii) analyze the sound data collected from the user environment; (iii) identify, based upon the analysis, a noise characteristic associated with the sound data and a duration of the sound data; (iv) compare the noise characteristic and the duration to a predetermined noise threshold; (v) determine whether the sound data represents unsafe noise conditions based upon the comparison; and/or (vi) notify the client device by sending an alert when the sound data is determined to represent unsafe noise conditions. The client device may generate at least one of an audible alert, a haptic alert, and a visible alert in response.

Machine Learning & Other Matters

The computer-implemented methods discussed herein may include additional, less, or alternate actions, including those discussed elsewhere herein. The methods may be implemented via one or more local or remote processors, transceivers, servers, and/or sensors (such as processors, transceivers, servers, and/or sensors mounted on vehicles or mobile devices, or associated with smart infrastructure or remote servers), and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

A processor or a processing element may be trained using supervised or unsupervised machine learning, and the machine learning program may employ a neural network, which may be a convolutional neural network, a deep learning neural network, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as image, mobile device, vehicle telematics, autonomous vehicle, and/or intelligent home telematics data. The machine learning programs may utilize deep learning algorithms that may be primarily focused on pattern recognition, and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or machine learning.

In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs.

Additional Considerations

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Wash.). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes. The present embodiments may enhance the functionality and functioning of computers and/or computer systems.

As used herein, an element or step recited in the singular and preceded by the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A computer-based method for assessing noise at a user environment, the method performed using a sound analysis computing system comprising at least one processor in communication with at least one memory device, the method comprising:

receiving, from a client device associated with a user, sound data collected from a user environment, wherein the user is located within the user environment;

analyzing the sound data collected from the user environment;

identifying, based upon the analyzing, a first noise characteristic and a second noise characteristic associated with the sound data and a first duration associated with the first noise characteristic and a second duration associated with the second noise characteristic, wherein the second noise characteristic is subsequent to the first noise characteristic;

comparing the first and second noise characteristics and the first and second noise durations to a first predetermined noise threshold associated with a first predetermined noise duration and a second predetermined noise threshold associated with a second predetermined noise duration;

determining whether the sound data represents unsafe noise conditions based upon the comparison;

continuing to collect sound data if the sound data is determined to not represent unsafe noise conditions; and notifying the client device when the sound data is determined to represent unsafe noise conditions, wherein the client device generates at least one of an audible alert, a haptic alert, and a visible alert in response.

2. The computer-based method in accordance with claim 1, wherein the first noise characteristic and the second noise characteristic include a decibel level associated with the sound data.

3. The computer-based method in accordance with claim 2, wherein the first predetermined noise threshold and the second predetermined noise characteristic vary at least partially as a function of decibel level and the associated duration.

4. The computer-based method in accordance with claim 1 further comprising:

receiving sound data associated with the user collected from a plurality of user environments;

identifying, based upon the analyzing, a plurality of noise characteristics associated with the sound data and a total duration of the sound data, wherein each noise characteristic of the plurality of noise characteristics is associated with a respective time increment of the total duration;

comparing the plurality of noise characteristics and the total duration to at least one of the first and second predetermined noise thresholds; and generating a noise report associated with the user based upon the comparison to facilitate identification of user environments having unsafe noise conditions.

5. The computer-based method in accordance with claim 4, further comprising transmitting the noise report to an insurance computing device for a risk assessment associated with the user.

6. The computer-based method in accordance with claim 4, wherein receiving sound data associated with the user collected from the plurality of user environments further comprises receiving location data associated with the client device for the total duration of the sound data, wherein each user environment of the plurality of user environments is identifiable in the noise report based at least partially upon the location data and the respective time increments.

7. The computer-based method in accordance with claim 1 further comprising:
receiving additional sound data associated with a plurality of users;
analyzing the additional sound data;
identifying, based upon the analysis, a respective noise characteristic and a respective duration associated with each user of the plurality of users from the additional sound data;
aggregating the respective noise characteristics and the respective durations of the additional sound data to generate an aggregated noise characteristic and an aggregated duration;
comparing the first and second noise characteristics and the first and second durations by the client device to the aggregated noise characteristic and the aggregated duration; and
generating a noise report associated with the user based at least partially upon the comparison.

8. The computer-based method in accordance with claim 7, wherein the aggregated duration is the same as at least one of the first and second durations.

9. A computer system for assessing noise at a user environment, the computer system comprising:
at least one processor; and
a non-transitory, tangible, computer-readable storage medium having instructions stored thereon that, in response to execution by the at least one processor, cause the at least one processor to perform operations comprising:
receiving, from a client device associated with a user, sound data collected from a user environment, wherein the user is located within the user environment;
analyzing the sound data collected from the user environment;
identifying, based upon the analyzing, a first noise characteristic and a second noise characteristic associated with the sound data and a first duration associated with the first noise characteristic and a second duration associated with the second noise characteristic, wherein the second noise characteristic is subsequent to the first noise characteristic;
comparing the first and second noise characteristics and the first and second noise durations to a first predetermined noise threshold associated with a first predetermined noise duration and a second predetermined noise threshold associated with a second predetermined noise duration;
determining whether the sound data represents unsafe noise conditions based upon the comparison;
continuing to collect sound data if the sound data is determined to not represent unsafe noise conditions; and
notifying the client device when the sound data is determined to represent unsafe noise conditions, wherein the client device generates at least one of an audible alert, a haptic alert, and a visible alert in response.

10. The computer system in accordance with claim 9, wherein the first noise characteristic and the second noise characteristic include a decibel level associated with the sound data.

11. The computer system in accordance with claim 10, wherein the first predetermined noise threshold varies and the second predetermined noise characteristic vary at least partially as a function of decibel level and the associated duration.

12. The computer system in accordance with claim 9, wherein the at least one processor is further configured to perform operations comprising:
receiving sound data associated with the user collected from a plurality of user environments;
identifying, based upon the analyzing, a plurality of noise characteristics associated with the sound data and a total duration of the sound data, wherein each noise characteristic of the plurality of noise characteristics is associated with a respective time increment of the total duration;
comparing the plurality of noise characteristics and the total duration to at least one of the first and second predetermined noise thresholds; and
generating a noise report associated with the user based upon the comparison to facilitate identification of user environments having unsafe noise conditions.

13. The computer system in accordance with claim 12, wherein the at least one processor is further configured to perform operations comprising transmitting the noise report to an insurance computing device for a risk assessment associated with the user.

14. The computer system in accordance with claim 12, wherein the at least one processor is further configured to perform operations comprising receiving location data associated with the client device for the total duration of the sound data, wherein each user environment of the plurality of user environments is identifiable in the noise report based at least partially upon the location data and the respective time increments.

15. The computer system in accordance with claim 9, wherein the at least one processor is further configured to perform operations comprising:
receiving additional sound data associated with a plurality of users;
analyzing the additional sound data;
identifying, based upon the analysis, a respective noise characteristic and a respective duration associated with each user of the plurality of users from the additional sound data;
aggregating the respective noise characteristics and the respective durations of the additional sound data to generate an aggregated noise characteristic and an aggregated duration;
comparing the first and second noise characteristics and the first and second durations by the client device to the aggregated noise characteristic and the aggregated duration; and
generating a noise report associated with the user based at least partially upon the comparison.

16. The computer system in accordance with claim 15, wherein the aggregated duration is the same as at least one of the first and second duration.

17. A non-transitory computer readable medium that includes computer executable instructions for assessing noise at a user environment, wherein when executed by a sound analysis computing system comprising at least one processor in communication with at least one memory device, the computer executable instructions cause the sound analysis computing system to:
receive, from a client device associated with a user, sound data collected from a user environment, wherein the user is located within the user environment;

analyze the sound data collected from the user environment;

identify, based upon the analysis, a first noise characteristic and a second noise characteristic associated with the sound data and a first duration associated with the first noise characteristic and a second duration associated with the second noise characteristic, wherein the second noise characteristic is subsequent to the first noise characteristic;

compare the first and second noise characteristics and the first and second noise durations to a first predetermined noise threshold associated with a first predetermined noise duration and a second predetermined noise threshold associated with a second predetermined noise duration;

determine whether the sound data represents unsafe noise conditions based upon the comparison;

continue to collect sound data if the sound data is determined to not represent unsafe noise conditions; and notify the client device when the sound data is determined to represent unsafe noise conditions, wherein the client device generates at least one of an audible alert, a haptic alert, and a visible alert in response.

18. The non-transitory computer readable medium of claim 17, wherein the first noise characteristic and the second noise characteristic include a decibel level associated with the sound data.

19. The non-transitory computer readable medium of claim 18, wherein the first determined noise threshold and the second predetermined noise characteristic vary at least partially as a function of decibel level and the associated duration.

20. The non-transitory computer readable medium of claim 17, wherein the computer executable instructions further cause the sound analysis computing system to:

receive sound data associated with the user collected from a plurality of user environments;

identify, based upon the analysis, a plurality of noise characteristics associated with the sound data and a total duration of the sound data, wherein each noise characteristic of the plurality of noise characteristics is associated with a respective time increment of the total duration;

compare the plurality of noise characteristics and the total duration to at least one of the first and second predetermined noise thresholds; and generate a noise report associated with the user based upon the comparison to facilitate identification of user environments having unsafe noise conditions.

21. The non-transitory computer readable medium of claim 20, wherein the computer executable instructions further cause the sound analysis computing system to transmit the noise report to an insurance computing device for a risk assessment associated with the user.

22. The non-transitory computer readable medium of claim 20, wherein the computer executable instructions further cause the sound analysis computing system to receive location data associated with the client device for the total duration of the sound data, wherein each user environment of the plurality of user environments is identifiable in the noise report based at least partially upon the location data and the respective time increments.

23. The non-transitory computer readable medium of claim 17, wherein the computer executable instructions further cause the sound analysis computing system to:

receive additional sound data associated with a plurality of users;

analyze the additional sound data;

identify, based upon the analysis, a respective noise characteristic and a respective duration associated with each user of the plurality of users from the additional sound data;

aggregate the respective noise characteristics and the respective durations of the additional sound data to generate an aggregated noise characteristic and an aggregated duration;

compare the first and second noise characteristics and the first and second durations by the client device to the aggregated noise characteristic and the aggregated duration; and generate a noise report associated with the user based at least partially upon the comparison.

24. The non-transitory computer readable medium of claim 23, wherein the aggregated duration is the same as at least one of the first and second durations.

* * * * *